United States Patent [19]

Chou et al.

[11] Patent Number: 5,252,756
[45] Date of Patent: Oct. 12, 1993

[54] PROCESS FOR PREPARING BETA-ANOMER ENRICHED 2-DEOXY-2,2-DIFLUORO-D-RIBOFURANO-SYL-ARYLSULFONATES

[75] Inventors: Ta-Sen Chou; Charles D. Jones, both of Indianapolis, Ind.

[73] Assignee: Eli Lilly and Company, Indianapolis, Ind.

[21] Appl. No.: 902,143

[22] Filed: Jun. 22, 1992

[51] Int. Cl.$^5$ .............................. C07D 307/20
[52] U.S. Cl. ........................... 549/476; 549/478
[58] Field of Search ............... 549/475, 476, 478

[56] References Cited

U.S. PATENT DOCUMENTS 4,526,988  7/1985  Hertel ................... 549/313
4,965,374  10/1990  Chou et al. ............. 549/313

OTHER PUBLICATIONS

Brewsfer & McEwen *Orgnaic Chemistry* pp. 528–529, (1961).

*Primary Examiner*—Alan L. Rotman
*Assistant Examiner*—Amelia A. Owens
*Attorney, Agent, or Firm*—Sidney Persley; Leroy Whitaker

[57] ABSTRACT

A stereoselective process for preparing 2-deoxy-2,2-difluoro-D-ribofuranosyl beta-anomer enriched aryl sulfonates or substituted arylsulfonates involving reacting a lactol with an acid scavenger and a sulfonating reagent in an inert solvent.

11 Claims, No Drawings

PROCESS FOR PREPARING BETA-ANOMER ENRICHED 2-DEOXY-2,2-DIFLUORO-D-RIBOFURANOSYL-ARYLSULFONATES

BACKGROUND OF THE INVENTION

Field of the Invention

This invention pertains to a process for making 2-deoxy-2,2-difluoro-D-ribofuranosyl-1-β-arylsulfonates for use as intermediates in the preparation of known anti-neoplastic and/or anti-viral agents.

State of the Art

Fluorine substitution has been investigated extensively in drug research and biochemistry as a means of enhancing the biological activity and increasing the chemical or metabolic stability of nucleosides. The replacement of a hydrogen by fluorine in a bioactive molecule is expected to cause minimal steric pertubations with respect to the molecule's mode of binding to receptors or enzymes and aid in overcoming the chemical and enzymatic instability problems of nucleosides. Deoxydifluoronucleosides are typically synthesized by coupling a difluororibofuranosyl derivative with a silylated purine or pyrimidine nucleobase.

U.S. Pat. No. 4,526,988 describes a process for making 3,5-hydroxy-protected 2-deoxy-2,2-difluororibofuranosyl-1-methanesulfonate by reacting 3,5-bis(t-butyldimethylsilyloxy) hydroxy protected 2-deoxy-2,2-difluororibofuranose dissolved in dichloromethane with methanesulfonyl chloride, in an equimolar amount of a suitable acid scavenger such as triethylamine for 3 hours at about 25° C. The resulting product is coupled with a purine or pyrimidine base to form an anomeric mixture of nucleosides.

There continues to be a need for a stereoselective process for preparing beta-anomer enriched 3,5-hydroxy protected 2-deoxy-2,2-difluoro-D-ribofuranosyl-1-arylsulfonates for use as intermediates in the synthesis of 1-α-halo-2-deoxy-2,2-difluoro D-ribofuranosyl derivatives, as described in Pending, U.S. patent application Ser. No. 07/902,306, filed contemporaneously herewith, or as intermediates in coupling reactions to make alpha nucleosides.

Accordingly, one object of the present invention is to provide a stereoselective process for preparing beta-anomer enriched 2-deoxy-2,2-difluoro-D-ribofuranosyl-1-arylsulfonates.

Another object of the present invention is to provide a stereoselective process for preparing beta-anomer enriched 2-deoxy-2,2-difluoro-D-ribofuranosyl-1-arylsulfonates in high yield.

SUMMARY OF THE INVENTION

The present invention is a stereoselective process for preparing a beta-anomer enriched ribofuranosyl derivative of the formula

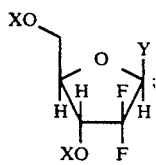

wherein each X is independently selected from hydroxy protecting groups and Y is selected from the group consisting of arylsulfonates and substituted arylsulfonates; comprising contacting a lactol of the formula

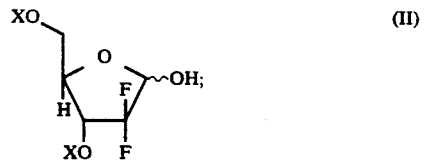

wherein X is as defined above, with an acid scavenger and a sulfonating reagent in an inert solvent.

DETAILED DESCRIPTION OF THE INVENTION

Throughout this document, all temperatures are in degrees Celsius, all proportions, percentages and the like, are in weight units and all mixtures are in volume units, except where otherwise indicated. Anomeric mixtures are expressed as a weight/weight ratio or as a percent. The term "xylenes" refers to all isomers of xylene and mixtures thereof. The term "lactol" alone or in combination refers to a 3,5-hydroxy-protected 2-deoxy-2,2-difluoro-D-ribofuranose. The term "halo" alone or in combination refers to chloro, iodo, fluoro and bromo halogens. The term "alkyl" alone or in combination refers to straight, cyclic and branched chain aliphatic hydrocarbon groups which preferably contain up to 7 carbon atoms, such as, methyl, ethyl, n-propyl, isopropyl, n-butyl, t-butyl, n-pentyl, n-hexyl, 3-methylpentyl groups and the like or substituted straight, cyclic and branched chain aliphatic hydrocarbons such as chloroethane, 1,2-dichloroethane, trifluoromethane and the like. The term "alkoxy" alone or in combination refers to compounds of the general formula RO; wherein R is an alkyl defined above. The term "aryl" alone or in combination refers to carbocyclic and heterocyclic compounds such as phenyl, naphthyl, thienyl and substituted derivatives thereof. The term "aromatic" alone or in combination refers to benzene-like structures containing $(4\pi+2)$ delocalized electrons. The term "sulfonate" alone or in combination refers to compounds of the general formula $BSO_3$, wherein B is an aryl group as defined above. The term "substituted" alone or in combination refers to the replacement of hydrogen or a common moiety by one or more groups selected from cyano, halo, carboalkoxy, aryl, nitro, alkoxy, alkyl and dialkyl amino. The phrase "anomer enriched" alone or in combination refers to an anomeric mixture wherein the ratio of a specified anomer is greater than 1:1 and includes substantially pure anomer.

Lactol starting materials suitable for use in the present process are described in U.S. Pat. No. 4,963,374, Chou. In the present process, the lactol is combined with an acid scavenger and a sulfonating reagent in an inert solvent.

Suitable acid scavengers are selected from the group consisting of trialkylamines such as trimethylamine, triethylamine, tripropylamine, triisopropylamine, triisobutylamine, tributylamine, diisopropylethylamine, dimethylethylamine, diethylmethylamine, N,N-dimethylaminopyridine, N-methylmorpholine, N,N-dimethylbenzylamine, and mixtures thereof. The acid scavenger preferably has a pKa of from about 8 to about 20 and is employed in at least an equimolar amount, relative to the amount of lactol employed; and more preferably employed in about 1.2 molar equivalents to about 2 molar equivalents.

The solvent may be selected from the group consisting of toluene, acetone, anisole, dichloromethane, 1,2-dichloroethane, xylenes, glyme, tetrahydrofuran, 1-nitroethane, nitropropane, 2-nitropropane, dichlorofluoromethane, nitroethane, chloroform, and mixtures thereof; preferred are dichloromethane and chloroform.

A sulfonating reagent is added to the mixture to form a beta-anomer enriched ribofuranosyl-1-arylsulfonate of formula I.

Suitable sulfonating reagents may be selected from the group consisting of arylsulfonyl halides, substituted arylsulfonyl halides, arylsulfonyl anhydrides and substituted arylsulfonyl anhydrides. Substituted arylsulfonyl halides are selected from the group consisting of 2-nitrobenzenesulfonyl chloride, p-cyanobenzenesulfonyl 3-nitrobenzenesulfonyl chloride, 2,4-dinitrobenzenesulfonyl chloride, p-bromobenzenesulfonyl chloride, p-fluorobenzenesulfonyl chloride, 2,4,6-triisopropylbenzenesulfonyl chloride, 2,4,6-trimethylbenzenesulfonyl chloride, p-iodobenzenesulfonyl chloride, p-chlorobenzenesulfonyl chloride, p-methoxybenzenesulfonyl chloride, and p-toluenesulfonyl chloride; preferred are 2-nitrobenzenesulfonyl chloride, 3-nitrobenzenesulfonyl chloride, p-bromobenzenesulfonyl chloride, p-fluorobenzenesulfonyl chloride, and p-chlorobenzenesulfonyl chloride; most preferred is p-bromobenzenesulfonyl chloride. Preferred arylsulfonyl anhydrides are selected from benzene sulfonic acid anhydride and p-bromobenzenesulfonic acid anhydride. Preferred arylsulfonyl halides are selected from benzenesulfonyl chloride and 2-naphthylenesulfonyl chloride; more preferred is benzenesulfonyl chloride.

The hydroxy protecting groups (X) are known in the art and are described in Chapter 3 of *Protective Groups in Organic Chemistry*, McOmie Ed., Plenum Press, New York (1973), and Chapter 2 of *Protective Groups in Organic Synthesis*, Green, John, J. Wiley and Sons, New York (1981); preferred are ester forming groups such as formyl, acetyl, substituted acetyl, propionyl, butynyl, pivaloyl, 2-chloroacetyl, benzoyl, substituted benzoyl, phenoxycarbonyl, methoxyacetyl; carbonate derivatives such as phenoxycarbonyl, ethoxycarbonyl, t-butoxycarbonyl, vinyloxycarbonyl, 2,2,2-trichloroethoxycarbonyl and benzyloxycarbonyl; alkyl ether forming groups such as benzyl, diphenylmethyl, triphenylmethyl, t-butyl, methoxymethyl, tetrahydropyranyl, allyl, tetrahydrothienyl, 2-methoxyethoxy methyl; and silyl ether forming groups such as trialkylsilyl, trimethylsilyl, isopropyldialkylsilyl, alkyldiisopropylsilyl, triisopropylsilyl, t-butyldialkylsilyl and 1,1,3,3-tetraisopropyldisloxanyl; carbamates such as N-phenylcarbamate and N-imidazoyl carbamate; however more preferred are benzoyl, mono-substituted benzoyl and disubstituted benzoyl, acetyl, pivaloyl, triphenylmethyl ethers, and silyl ether forming groups, especially t-butyldimethylsilyl; while most preferred is benzoyl.

The temperature employed in the present process ranges from about room temperature to about the reflux temperature of the mixture. The present process is preferably carried out under atmospheric pressure and is substantially complete in about 30 minutes to about 24 hours.

The progress of the present conditions may be followed using high pressure liquid chromotography (HPLC) or NMR spectroscopy.

The following examples illustrate specific aspects of the present invention and are not intended to limit the scope thereof in any respect and should not be so construed.

EXAMPLE 1

Preparation of beta-anomer enriched 2,2-difluoro-2-deoxy-D-ribofuranosyl-3,5-di-O-benzoyl-1-(2,4,6-triisopropylbenzene)sulfonate.

To 100 mg of 2-deoxy-2,2-difluoro-D-ribofuranosyl-3,5-dibenzoate were added 2 ml of dichloromethane, 0.026 ml of triethylamine and 79.9 mg of 2,4,6-tri-isopropylbenzenesulfonyl chloride. After about 18 hours at room temperature the titled compound was formed in a beta to alpha ratio of 24:1, as determined by NMR spectroscopy.

To isolate the beta-sulfonate, the reaction mixture was diluted with dichloromethane and water. The layers were separated and the organic layer was washed with cold 1N HCl and dried over anhydrous magnesium sulfate. The resulting solution was concentrated to an oil. The yield of the beta and alpha sulfonate mixture was 100 percent.

EXAMPLE 2

Preparation of beta-anomer enriched 2,2-difluoro-2-deoxy-D-ribofuranosyl-3,5-di-O-benzoyl-1-(4-bromobenzene) sulfonate.

To 1.34 g of 2-deoxy-2,2-difluoro-D-ribofuranosyl-3,5-dibenzoate were added 35 ml of dichloromethane, 0.53 ml of triethylamine and 0.905 g of 4-bromobenzenesulfonyl chloride. After about 16 hours at room temperature the titled compound was formed in a beta to alpha ratio of 8.2:1, as determined by reversed phase HPLC.

To isolate the beta-sulfonate, the reaction mixture was diluted with dichloromethane and water. The layers were separated and the organic layer was washed with cold 1N HCl, aqueous sodium bicarbonate, saturated sodium chloride solution and water, then dried over anhydrous magnesium sulfate. The resulting solution was concentrated to an oily residue and allowed to crystallize. Following a recrystallization from ethyl acetate, the titled compound was obtained in a 72 percent yield; m.p. 121° C.–123° C.; Elemental Analysis: (Calc.) C: 51.56, H: 3.46, S: 5.50; (Actual) C: 51.29, H: 3.36, S: 5.44. QE 300 $^1$H NMR(CDCl$_3$) $\delta$=8.2(m, 4H, Ar-o), 7.69-7.4(m,10H, Ar-m and p), 6.11(d, 1H, 1-H), 5.88(m, 1H, 3-H), 4.57(m, 1H, 4-H) 4.5/4,.26(mm, 2H, 5-H).

The title compound was crystallized in the orthorhombic space group P2$_1$2$_1$2$_1$ with a unit cell having the dimensions a=6.933(1) $\theta$, b=14.361(4) Å, c=24.997(7) Å, and a calculated density of 1.594 g/cm$^3$. A total of 2015 reflections with 2$\theta$ less than 116.0° was measured on an automated four-circle x-ray diffractometer using monochromatic copper radiation. The structure was solved using direct methods and was refined by least-squares with anisotropic temperature factors for all atoms except hydrogen. All hydrogen atoms were included at calculated positions. The final R-factor was 0.053 for 1884 observed reflections.

EXAMPLE 3

Preparation of beta-anomer enriched 2,2-difluoro-2-deoxy-D-ribofuranosyl-3,5-di-O-benzoyl-1-(2,4,6-trimethylbenzene)sulfonate.

To 100 mg of 2-deoxy-2,2-difluoro-D-ribofuranosyl-3,5-dibenzoate were added 2 ml of dichloromethane, 0.036 ml of triethylamine and 57.7 mg of 2,4,6-trimethylbenzenesulfonyl chloride. After about 18 hours at room temperature the titled compound was formed in a beta to alpha ratio of 9.5:1, as determined by NMR spectroscopy.

To isolate the beta-sulfonate, the reaction mixture was diluted with dichloromethane and water. The layers were separated and the organic layer was washed with cold 1N HCl and water then dried over anhydrous magnesium sulfate. The resulting solution was concentrated to an oil. The yield of the alpha and beta sulfonate mixture was 91 percent.

EXAMPLE 4

Preparation of beta-anomer enriched 2,2-difluoro-2-deoxy-D-ribofuranosyl-3,5-di-O-benzoyl-1-(4-iodobenzene)sulfonate.

To 100 mg of 2-deoxy-2,2-difluoro-D-ribofuranosyl-3,5-dibenzoate were added 2 ml of dichloromethane, 0.026 ml of triethylamine and 79.9 mg of 4-iodobenzenesulfonyl chloride. After about 1 hour at room temperature the titled compound was formed in a beta to alpha ratio of 8.6:1, as determined by proton NMR.

To isolate the beta-sulfonate, the reaction mixture was diluted with dichloromethane and water. The layers were separated and the organic layer was washed with cold 1N HCl then dried over anhydrous magnesium sulfate. The resulting solution was concentrated to an oil. The yield of the beta and alpha sulfonate mixture, as determined by proton NMR, was 80 percent.

EXAMPLE 5

Preparation of beta-anomer enriched 2,2-difluoro-2-deoxy-D-ribofuranosyl-3,5-di-O-benzoyl-1-(4-chlorobenzene) sulfonate.

To 100 mg of 2-deoxy-2,2-difluoro-D-ribofuranosyl-3,5-dibenzoate were added 2 ml of dichloromethane, 0.026 ml of triethylamine and 55.7 mg of 4-chlorobenzenesulfonyl chloride. After about 1 hour at room temperature the titled compound was formed in a beta to alpha ratio of 6.1:1, as determined by NMR spectroscopy.

To isolate the beta-sulfonate, the reaction mixture was diluted with dichloromethane and water. The layers were separated and the organic layer was washed with cold 1N HCl, and dried over anhydrous magnesium sulfate. The resulting solution was concentrated to an oil. The yield of the titled compound, as determined by proton NMR, was 82 percent.

EXAMPLE 6

Preparation of beta-anomer enriched 2,2-difluoro-2-deoxy-D-ribofuranosyl-3,5-di-O-benzoyl-1-(4-methoxybenzene)sulfonate.

To 100 mg of 2-deoxy-2,2-difluoro-D-ribofuranosyl-3,5-dibenzoate were added 2 ml of dichloromethane, 0.026 ml of triethylamine and 55 mg of 4 methoxybenzenesulfonyl chloride. After about 1 hour at room temperature the titled compound was formed in a beta to alpha ratio of 9:1, as determined by proton NMR.

To isolate the beta-sulfonate, the reaction mixture was diluted with dichloromethane and water. The layers were separated and the organic layer was washed with cold 1N HCl, sodium carbonate, saturated sodium chloride and water then dried over magnesium sulfate. The resulting solution was concentrated to an oil. The yield of the alpha and beta sulfonate mixture, as determined by proton NMR analysis was 72 percent.

EXAMPLE 7

Preparation of beta-anomer enriched 2,2-difluoro-2-deoxy-D-ribofuranosyl-3,5-di-O-benzoyl-1-(2-nitrobenzene)sulfonate.

To 100 mg of 2-deoxy-2,2-difluoro-D-ribofuranosyl-3,5-dibenzoate were added 2 ml of dichloromethane, 0.042 ml of triethylamine and 64.4 mg of 2-nitrobenzenesulfonyl chloride. After about 2 hours at room temperature the titled compound was formed in a beta to alpha ratio of 8:1, as determined by NMR spectroscopy.

To isolate the beta-sulfonate, the reaction mixture was diluted with dichloromethane and water. The layers were separated and the organic layer was washed with cold 1N HCl and dried over anhydrous magnesium sulfate. The resulting solution was concentrated to an oil.

EXAMPLE 8

Preparation of beta-anomer enriched 2,2-difluoro-2-deoxy-D-ribofuranosyl-3,5-di-O-benzoyl-1-(3-nitrobenzene)sulfonate.

To 100 mg of 2-deoxy-2,2-difluoro-D-ribofuranosyl-3,5-dibenzoate were added 2 ml of dichloromethane, 0.042 ml of triethylamine and 64.4 mg of 3-nitrobenzenesulfonyl chloride. After about 2 hours at room temperature the titled compound was formed in a beta to alpha ratio of 8.5:1, as determined by NMR spectroscopy.

To isolate the beta-sulfonate the reaction mixture was diluted with dichloromethane and water. The layers were separated and the organic layer was washed with cold 1N HCl and dried over anhydrous magnesium sulfate. The resulting solution was concentrated to an oil.

EXAMPLE 9

Preparation of beta-anomer enriched 2,2-difluoro-2-deoxy-D-ribofuranosyl-3,5-di-O-benzoyl-1-(4-fluorobenzene)sulfonate.

To 100 mg of 2-deoxy-2,2-difluoro-D-ribofuranosyl-3,5-dibenzoate were added 2 ml of dichloromethane, 0.042 ml of triethylamine and 56.5 mg of 4-fluorobenzenesulfonyl chloride. After 2 hours at room temperature the titled compound was formed in a beta to alpha ratio of 8.4:1, as determined by reversed phase HPLC.

To isolate the beta-sulfonate, the reaction mixture was diluted with dichloromethane and water. The layers were separated and the organic layer was washed with 1N HCl and dried over anhydrous magnesium sulfate. The resulting solution was concentrated to an oil. The yield of the beta and alpha sulfonate mixture, as determined by NMR spectroscopy, was 85 percent.

EXAMPLE 10

Preparation of beta-anomer enriched 2,2-difluoro-2-deoxy-D-ribofuranosyl-3,5-di-O-benzoyl-1-(4-methylbenzene) sulfonate.

To 100 mg of 2-deoxy-2,2-difluoro-D-ribofuranosyl-3,5-dibenzoate were added 2 ml of dichloromethane, 0.042 ml of triethylamine and 55.3 mg of p-toluenesulfonyl chloride. After 2 hours at room temperature the titled compound was formed in a beta to alpha ratio of 7.2:1, as determined by reversed phase HPLC.

To isolate the beta-sulfonate, the reaction mixture was diluted with dichloromethane and water. The layers were separated and the organic layer was washed with cold 1N HCl and dried over anhydrous magnesium sulfate. The resulting solution was concentrated to an oil. The yield of the beta and alpha sulfonate mixture, as determined by NMR spectroscopy, was 100 percent.

EXAMPLE 11

Preparation of beta-anomer enriched 2,2-difluoro-2-deoxy-D-ribofuranosyl 3,5-di-O-benzoyl-1-benzenesulfonate.

To 100 mg of 2-deoxy-2,2-difluoro-D-ribofuranosyl-3,5-dibenzoate were added 2 ml of dichloromethane, 0.042 ml of triethylamine and 51.3 mg of benzenesulfonyl chloride. After 2 hours at room temperature the titled compound was formed in a beta to alpha ratio of 7.4:1, as determined by reversed phase HPLC.

To isolate the beta-sulfonate, the reaction mixture was diluted with dichloromethane and water. The layers were separated and the organic layer was washed with cold 1N HCl and dried over anhydrous magnesium sulfate. The resulting solution was concentrated to an oil. The yield of the beta and alpha sulfonate mixture, as determined by NMR spectroscopy, was 100 percent.

EXAMPLE 12

Preparation of beta-anomer enriched 2,2-difluoro-2-deoxy-D-ribofuranosyl-3,5-di-O-benzoyl-1-(2-naphthylene)sulfonate.

To 100 mg of 2-deoxy-2,2-difluoro-D-ribofuranosyl-3,5-dibenzoate were added 1 ml of chloroform-d, 0.055 ml of triethylamine and 72 mg of 2-naphthylenesulfonyl chloride. After 3 hours at room temperature the titled compound was formed in a beta to alpha ratio of 7:1, as determined by HPLC.

To isolate the beta-sulfonate, the reaction mixture was diluted with dichloromethane and water. The layers were separated and the organic layer was washed with cold 1N HCl and dried over anhydrous magnesium sulfate. The resulting solution was concentrated to an oil.

EXAMPLE 13

Preparation of beta-anomer enriched 2,2-difluoro-2-deoxy-D-ribofuranosyl-3,5-di-O-benzoyl-1-(p-bromobenzene) sulfonate.

To 7.56 g of 2-deoxy-2,2-difluoro-D-ribofuranosyl-3,5-dibenzoate were added 50 ml of 1,2-dichloroethane and 3.06 ml triethylamine at room temperature under a nitrogen atmosphere. Next, 10.3 g of solid (p-bromobenzene)sulfonic anhydride were added over 2 minutes along with 25 ml of 1,2-dichloroethane. After about 2.5 hours at room temperature the titled compound formed in a beta to alpha ratio of 6:1, as determined by reversed phase HPLC. The yield of the alpha and beta sulfonate mixture, as determined by reversed phase HPLC, was 100 percent.

The present invention has been described in detail, including the preferred embodiments thereof. However, it will be appreciated that those skilled in the art, upon consideration of the present disclosure, may make modifications and/or improvements on this invention that fall within the scope and spirit of the invention as set forth in the following claims.

What is claimed is:

1. A stereoselective process for preparing a beta-anomer enriched ribofuranosyl derivative of the formula

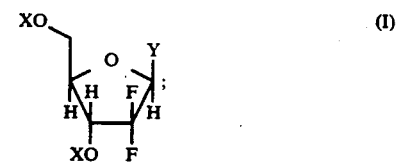

wherein X each is independently selected from hydroxy protecting groups and Y is selected from the group consisting of arylsulfonate and substituted arylsulfonate; comprising contacting a lactol of the formula

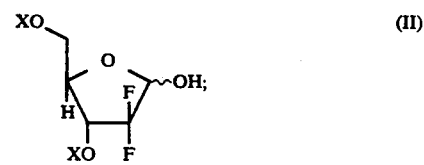

wherein X is as defined above, with an acid scavenger and a sulfonating reagent in an inert solvent.

2. The process of claim 1 wherein the acid scavenger is selected from the group consisting of trimethylamine, triethylamine, triisopropylamine, tri-n-propylamine, tributylamine, tri-n-butylamine, diisopropylethylamine, dimethylethylamine, diethylmethylamine, N-methylmorpholine, N,N-dimethylbenzylamine, and mixtures thereof.

3. The process of claim 2 wherein the acid scavenger is triethylamine.

4. The process of claim 2 wherein the acid scavenger has a pKa of from about 8 to about 20.

5. The process of claim 1 wherein the amount of acid scavenger is about 1 molar equivalent to about 2 molar equivalents.

6. The process of claim 1 wherein the sulfonating reagent is selected from the group consisting of arylsulfonyl halides, substituted arylsulfonyl halides, arylsulfonyl anhydrides and substituted arylsulfonyl anhydrides.

7. The process of claim 6 wherein the substituted arylsulfonyl halide is selected from the group consisting of 2-nitrobenzenesulfonyl chloride, 3-nitrobenzenesulfonyl chloride, 2,4-dinitrobenzenesulfonyl chloride, p-bromobenzenesulfonyl chloride, p-fluorobenzenesulfonyl chloride, 2,4,6-triisopropylbenzenesulfonyl chloride, 2,4,6-trimethylbenzenesulfonyl chloride, p-iodobenzenesulfonyl chloride, p-chlorobenzenesulfonyl chloride, 4-methoxybenzenesulfonyl chloride, and p-methylbenzenesulfonyl chloride.

8. The process of claim 6 wherein the arylsulfonyl halide is selected from benzenesulfonyl chloride, p-bromobenzenesulfonyl chloride and 2-naphthylenesulfonyl chloride.

9. The process of claim 1 wherein the solvent is selected from the group consisting of toluene, acetone, anisole, dichloromethane, 1,2-dichloroethane, xylenes, glyme, tetrahydrofuran, 1-nitropropane, 2-nitropropane, dichlorofluoromethane, nitroethane, chloroform, and mixtures thereof.

10. The process of claim 9 wherein the solvent is selected from the group consisting of dichloromethane, chloroform, and mixtures thereof.

11. The process of claim 10 wherein the solvent is dichloromethane.

* * * * *

UNITED STATES PATENT AND TRADEMARK OFFICE
CERTIFICATE OF CORRECTION

PATENT NO.    : 5,252,756

DATED         : October 12, 1993

INVENTOR(S)   : Ta-Sen Chou, et al.

It is certified that an error appears in the above-identified patent and that said Letters Patent is hereby corrected as shown below:

Column 1, line 43, "difluoro D" should read --difluoro-D--.

Column 1, line 44, "patent application" should read --Patent Application--.

Column 2, line 46, "BS03" should read --BSO3--.

Column 3, line 7, "nitropropane" should read --1-nitropropane--.

Column 4, line 53, "Ar-m and p" should read --Ar-m and p--.

Column 4, line 53, "Ar-o" should read --Ar-o--.

Column 7, line 16, "D-ribofuranosyl 3,5-di" should read --D-ribofuranosyl-3,5-di--.

Signed and Sealed this

Sixth Day of December, 1994

Attest:

BRUCE LEHMAN

Attesting Officer    Commissioner of Patents and Trademarks